United States Patent [19]

Harris

[11] Patent Number: 4,632,096
[45] Date of Patent: Dec. 30, 1986

[54] AUTOMATICALLY RELEASING KNEE BRACE

[76] Inventor: Adam I. Harris, 625 N. Arden Dr., Beverly Hills, Calif. 90210

[21] Appl. No.: 764,600

[22] Filed: Aug. 12, 1985

[51] Int. Cl.$^4$ .............................................. A61F 5/00
[52] U.S. Cl. .................................. 128/80 F; 128/80 C
[58] Field of Search ................. 128/80 F, 80 R, 80 C, 128/80 E, 80 G, 88; 623/44

[56] References Cited

U.S. PATENT DOCUMENTS

| | | | |
|---|---|---|---|
| 2,512,826 | 6/1950 | Clark | 128/80 F |
| 2,522,853 | 9/1950 | Black | 128/80 F |
| 2,594,227 | 4/1952 | Smith | 128/80 F X |
| 2,883,982 | 4/1959 | Rainey | 128/80 F |
| 2,943,622 | 7/1960 | Nelson | 128/80 F |
| 4,456,003 | 6/1984 | Allard et al. | 128/80 F |

FOREIGN PATENT DOCUMENTS

| | | | |
|---|---|---|---|
| 948372 | 1/1949 | France | 128/80 F |
| 1213855 | 11/1970 | United Kingdom | 128/80 F |

Primary Examiner—Clifford D. Crowder
Attorney, Agent, or Firm—Spensley Horn Jubas & Lubitz

[57] ABSTRACT

An orthosis for the leg which releases automatically upon a preselected dorsiflexion of the ankle followed by a preselected plantar flexion of the ankle is described. The orthosis has an upper member for securing to the upper part of the leg and a lower member for securing to the lower part of the leg, the upper and lower members interconnected by a pivoting means for placement at the knee. In a preferred embodiment, the orthosis is provided with a lock hinge which spans the pivoting means and locks the upper member and lower member when the leg approaches extension during a gait cycle, thereby providing stability when the foot of the braced leg strikes the ground. An automatically releasing mechanism is responsive to a preselected plantar flexion of the ankle occurring during a gait cycle after a preselected dorsiflexion of the ankle has occurred. This sequence permits the upper and lower members to be released when the required plantar flexion has taken place only once during each gait cycle, notwithstanding that the same plantar flexion of the ankle typically occurs twice during a gait cycle. In a preferred embodiment, the motion of the foot is communicated to a T-Bar which slides in a guideway comprising adjacent communicating channels. Achievement of the required dorsiflexion causes the T-Bar to be directed from the first channel into the second channel. Subsequent plantar flexion of the required amount causes the T-Bar to trigger a linkage in the second channel connected to the lock hinge for releasing the orthosis. The T-Bar is directed again into the first channel of the guideway for the next gait cycle.

19 Claims, 15 Drawing Figures

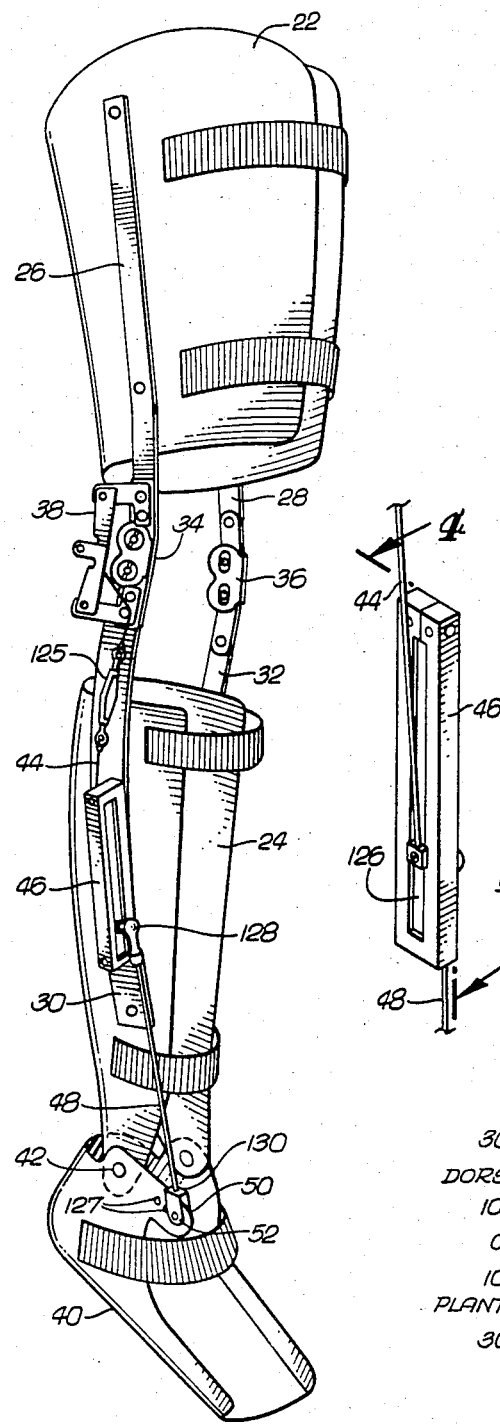
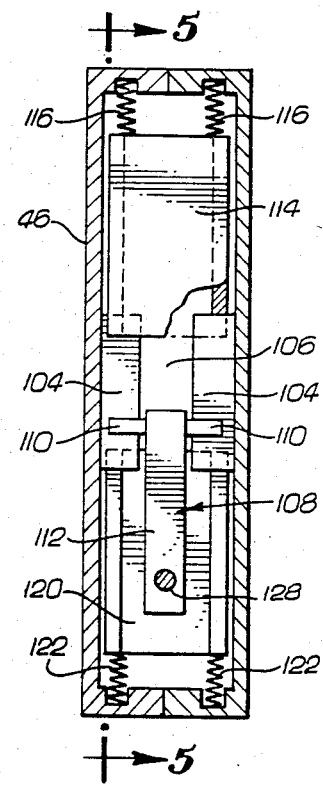
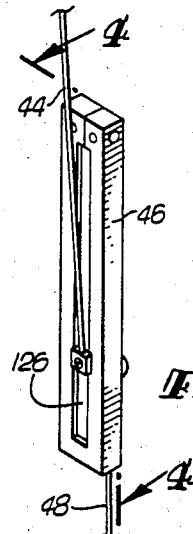
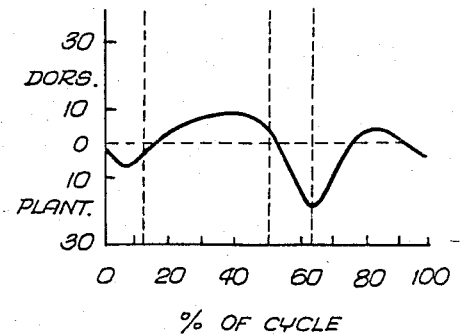

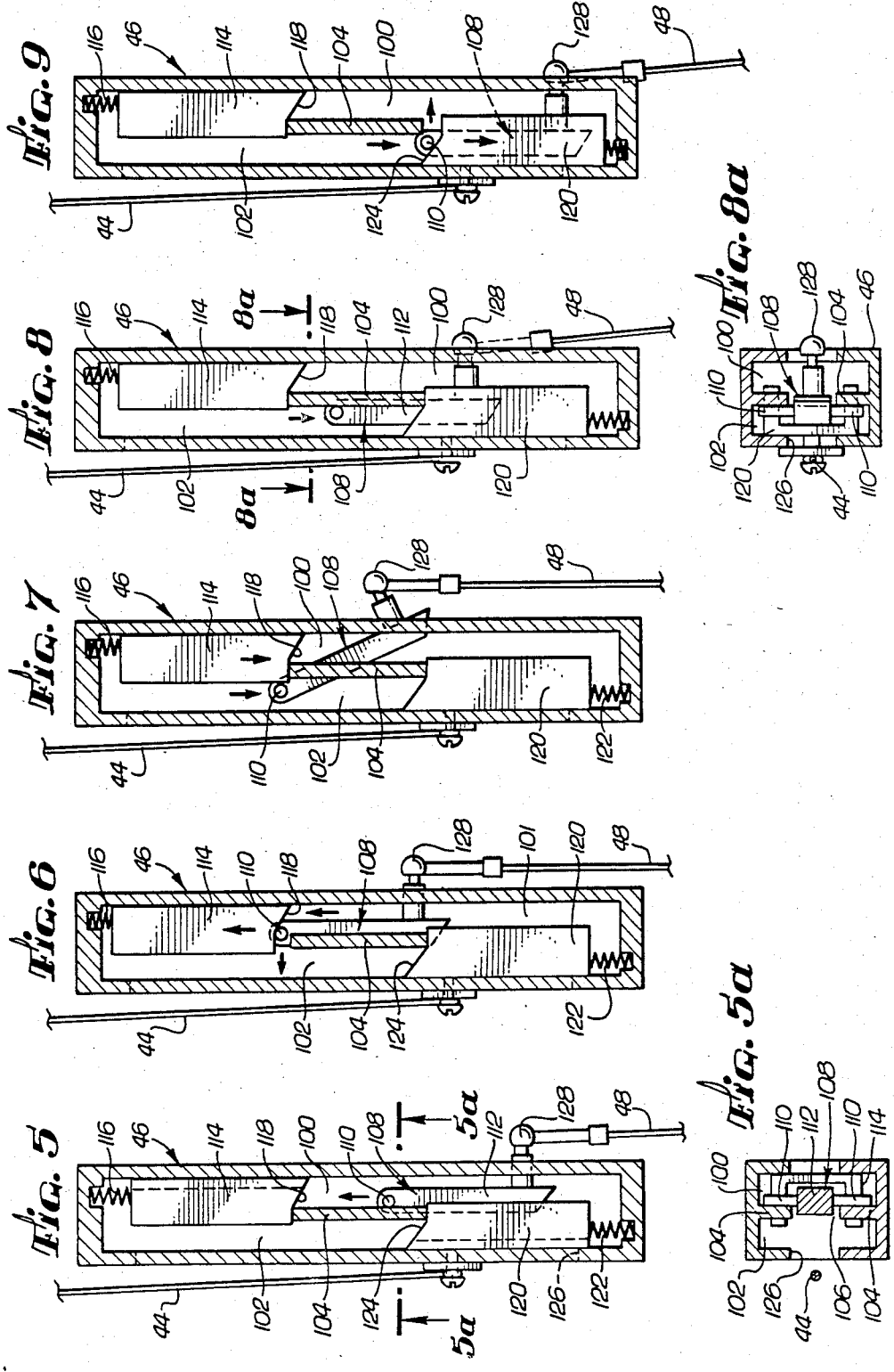

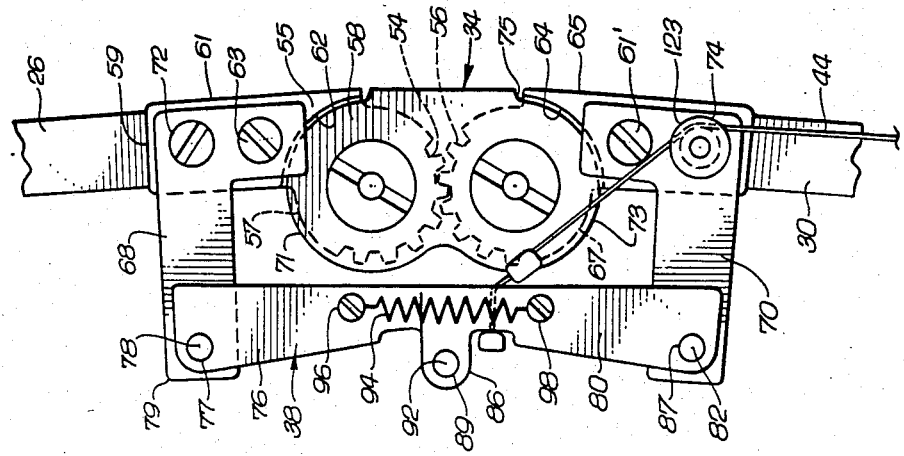
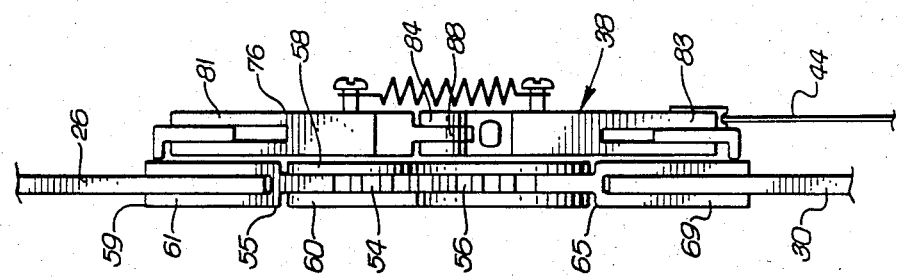
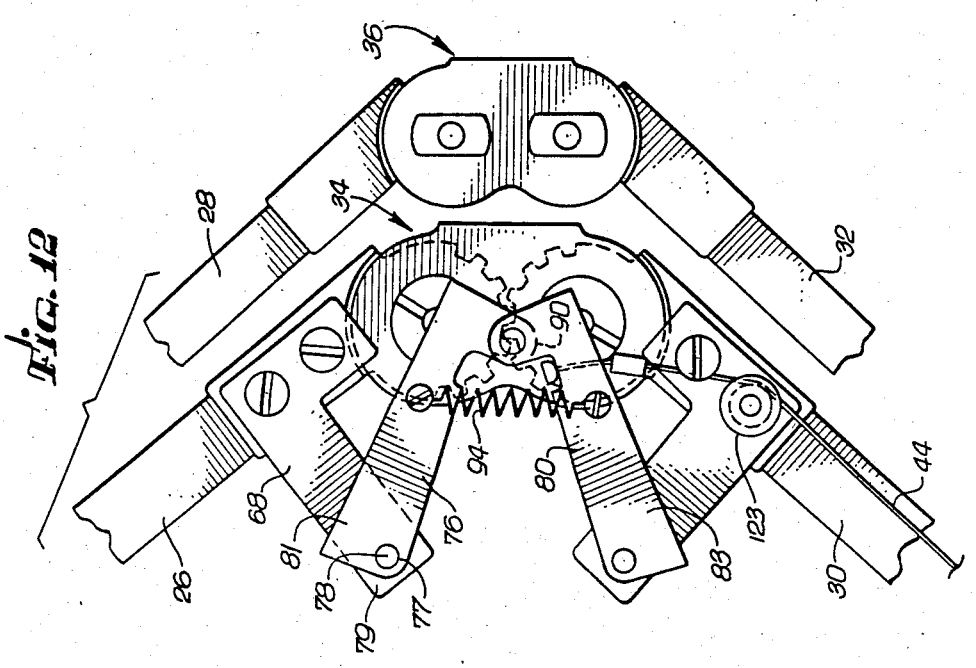

AUTOMATICALLY RELEASING KNEE BRACE

BACKGROUND OF THE INVENTION

1. Field of the Invention

This invention relates to an apparatus adapted to enable and/or to improve ambulation in persons afflicted with weakness or instability in the knee joint and in particular, with an apparatus that does so without maintaining the leg locked in extension during the entire gait cycle. The apparatus is designed to be especially useful for patients afflicted with Duchenne muscular dystrophy, but may also be used by patients who have suffered spinal cord or nerve root injuries or suffer from neurological or muscular disease and have a similar pattern of proximal weakness to that suffered by patients with muscular dystrophy, and also by patients with severe ligamentous damage at the knee who experience secondary loss of control of the knee.

2. Description of the Prior Art

Patients having Duchenne muscular dystrophy experience a loss in the power of the quadriceps muscles, and hence, knee control. Such patients, to compensate for weak quadriceps and gluteus maximus muscles, adopt a characteristic posture and gait which is awkward and leads to other problems. Specifically, these patients often develop lumbar lordosis, equinus posturing and anterior pelvic tilt. In the extreme the lordosis brings the line of force posterior to the hip. The equinus moves the distal end of the line of force forward. This in turn changes the usual torques about these joints.

In terms of the knee, the usual torque which tends towards flexion becomes a torque favoring extension. The ligaments then provide the limit on knee extension and the locked knee becomes a firm, albeit awkward support for ambulation. The conventional form of orthosis maintains the leg in extension during gait.

While the straight-legged brace is often prescribed, mechanical orthoses in which the knee is alternately mechanically locked and unlocked have been developed, in some cases as a spin-off from prosthetic technology.

The functioning of prior art mechanical orthoses and the difference and improvement over such represented by the present invention can be better understood with reference to the positions in dorsiflexion and plantar flexion assumed by the ankle during a normal gait cycle. FIG. 1, derived from data generated and reported by D. H. Sutherland in *Gait Disorders in Childhood and Adolescence* (Waverly Press, Inc. 1984), represents graphically the motion of a normal adult ankle during a gait cycle measured from foot strike to foot strike on the same side. The dotted vertical lines represent, respectively from left to right, foot flat, opposite foot strike and toe off.

As shown in FIG. 1, the ankle, during one gait cycle, goes through relative plantar flexion twice. To approximate normal gait, the leg should swing freely at the knee well before toe off, i.e., when the ankle is in a state of relatively small plantar flexion.

One recent approach to providing an orthosis for persons afflicted with weakness or instability of the knee is exemplified in U.S. Pat. No. 4,456,003 in which a pivotally mounted dog alternately interferes with a rotatable cog member, the axis of rotation of which corresponds to that for elongate members extending along the upper and lower parts of the leg and corresponding to a hypothetical pivot axis for the knee. This orthosis uses a unicentric hinge which does not closely approximate the axis of the knee.

The device disclosed in U.S. Pat. No. 4,456,003 is not a locking-type orthosis, i.e., the knee is not locked into extension during part of the gait cycle. Instead, a tension member is used so that a moment acting to extend the leg is created. The tension member is released by plantar flexion. As the person plantar flexes the ankle before swinging it forwardly through the air, the dog is withdrawn from its interfering relationship with the cog.

Since a single angle in plantar flexion releases the knee, the selection of this angle is problematic in that it must be selected to be greater than the plantar flexion undergone by the ankle shortly after foot strike and before foot flat.

Also the encouragement of plantar flexion may encourage the undesirable development of contractures. The encouragement of dorsiflexion, on the other hand, is considered therapeutic, especially in patients affected with Duchenne muscular dystrophy.

Another orthosis is described in U.S. Pat. No. 2,883,982. This orthosis provides a polycentric hinge including a gear means and a locking mechanism which is automatically released during dorsiflexion. With reference again to FIG. 1, the release of the locking mechanism during dorsiflexion would occur before the 50% point during the gait cycle i.e., before opposite foot strike. This is considered too early as weight and balance have not been established on the opposite foot.

Yet another orthosis is shown in French Pat. No. 948,372 which employs a unicentric hinge and locking mechanism which appears to be released during dorsiflexion. This orthosis would be subject to the same shortcomings as the orthosis described in U.S. Pat. No. 2,883,982.

SUMMARY OF THE INVENTION

It is an object of the present invention to provide an orthosis or brace for persons having a weak or unstable knee, such as persons suffering from Duchenne muscular dystrophy, and in particular to provide an orthosis that enables those persons to walk with a gait approximating normal gait.

It is another object of the present invention to provide a brace for such persons that holds the knee rigid for only part of the gait cycle. Around the time that the foot (on the leg that is braced) is striking the ground and weight remains on that leg, the orthosis is locked. The knee is permitted to flex during portions of the swing phase so that normal gait may be approximated.

It is a third object of the present invention to provide an orthosis or brace which requires for release of its locking mechanism a predetermined dorsiflexion of the ankle followed by subsequent plantar flexion in order to provide a more suitable release time for the locking mechanism than can be obtained using a single angle either of dorsiflexion or plantar flexion.

It is a fourth object of the present invention to provide a knee brace which is therapeutic in that it encourages dorsiflexion of the ankle and helps to avoid the onset of contractures, which may help to delay or inhibit the effect of some of the infirmities associated with diseases such as Duchenne muscular dystrophy.

Yet a further object of the present invention is to achieve all of the above objects in a brace which can be mechanically controlled, inexpensive, and streamlined so that its presence is not readily apparent to anyone other than the wearer.

To achieve these objects, the present invention provides, in a preferred embodiment, a mechanically controlled, automatic releasing free knee brace, the locking mechanism for which is built into a long-leg, knee-ankle-foot orthosis.

In the orthosis of the present invention, polycentric hinges having meshing gears are provided to couple the lateral and medial elongate members extending along the upper and lower parts of the leg. A lock hinge includes offset arms attached to the elongate members along one side in the vicinity of the lateral polycentric hinge coupling the members together. Pivoted members extending from each offset arm are coupled at a central axis of rotation which is posterior to the pivots connecting the members to the offset arms when the hinge is locked. In the fully extended or locked position, these members are stable and prevent the brace from flexing.

A pull cable connected near the central axis of rotation is for releasing the lock hinge. The pull cable is coupled to a movable spring-loaded trigger block in a range box located on the lower elongate member between the knee and the ankle of the patient. The range box comprises a dual channeled enclosure in which a T-bar actuating member circumlocutes between the channels during a gait cycle. The base of the T-bar is connected to one end of a throw arm, the other end of which is connected to a throw lever protruding anteriorly from the ankle portion of the foot piece of the brace.

Movement of the foot and ankle during a gait cycle causes the throw arm to move the T-bar within the range box. During the dorsiflexion of the late portion of the stance phase of a gait cycle, the T-bar moves upward in the first channel and is directed into the second channel. During the shortly succeeding plantar flexion of the early swing phase of the gait cycle, the T-bar tracks back in the second channel where it presses against the spring-loaded trigger block. The trigger block pulls on the pull cable which in turn pulls on the extended pivoted members of the lock hinge, allowing them to pivot and unlock the lock hinge thereby permitting the orthosis, and thus the knee it is bracing, to flex. This permits ambulation that may approximate normal gait to occur. During the late part of the swing phase of the gait cycle, the leg becomes almost fully extended. A spring connected between the two extended pivoted members of the lock hinge assists in pulling those members into alignment, locking the lock hinge and thus the knee prior to heel strike.

It will be appreciated from the foregoing brief description as well as from the more detailed description of the presently preferred embodiment that dorsiflexion followed by plantar flexion is necessasry to enable the T-bar to properly move within the range box and to actuate the trigger block to unlock the lock hinge.

BRIEF DESCRIPTION OF THE DRAWINGS

FIG. 1 is a graphical representation of the plantar flexion and dorsiflexion of the ankle of a typical adult during a single gait cycle measured from foot strike to foot strike on the same side.

FIG. 2 is a perspective view of the presently preferred embodiment of the present invention.

FIG. 3 is a perspective view of the posterior side of the range box of the presently preferred embodiment of the present invention.

FIG. 4 is a sectional longitudinal view of the range box of the presently preferred embodiment of the present invention taken along the lines 4—4 of FIG. 3.

FIGS. 5 through 9 are sectional longitudinal views of the range box. The views show the relative positions of the components in the range box at various times during a gait cycle as will be more particularly described. The views are taken along the lines 5—5 in FIG. 4.

FIGS. 5a and 8a are cross sectional views of the range box taken along the lines 5a—5a and 8a-8a respectively of FIGS. 5 and 8.

FIG. 10 is a side view of the polycentric hinge assembly and the lock hinge assembly used in the presently preferred embodiment of the present invention, with the lock hinge assembly in the locked state. Some components, not ordinarily visible in such view, are depicted by dashed lines.

FIG. 11 is an end view of the polycentric hinge assembly and the lock hinge assembly of FIG. 10 taken from the posterior side.

FIG. 12 is a side view of the polycentric hinge assembly and the lock hinge assembly of the presently preferred embodiment of the present invention with the lock hinge in the unlocked state. The polycentric hinge located on the opposite side of the knee to the lock hinge is shown in the background.

DESCRIPTION OF THE PREFERRED EMBODIMENT

Figure 13:
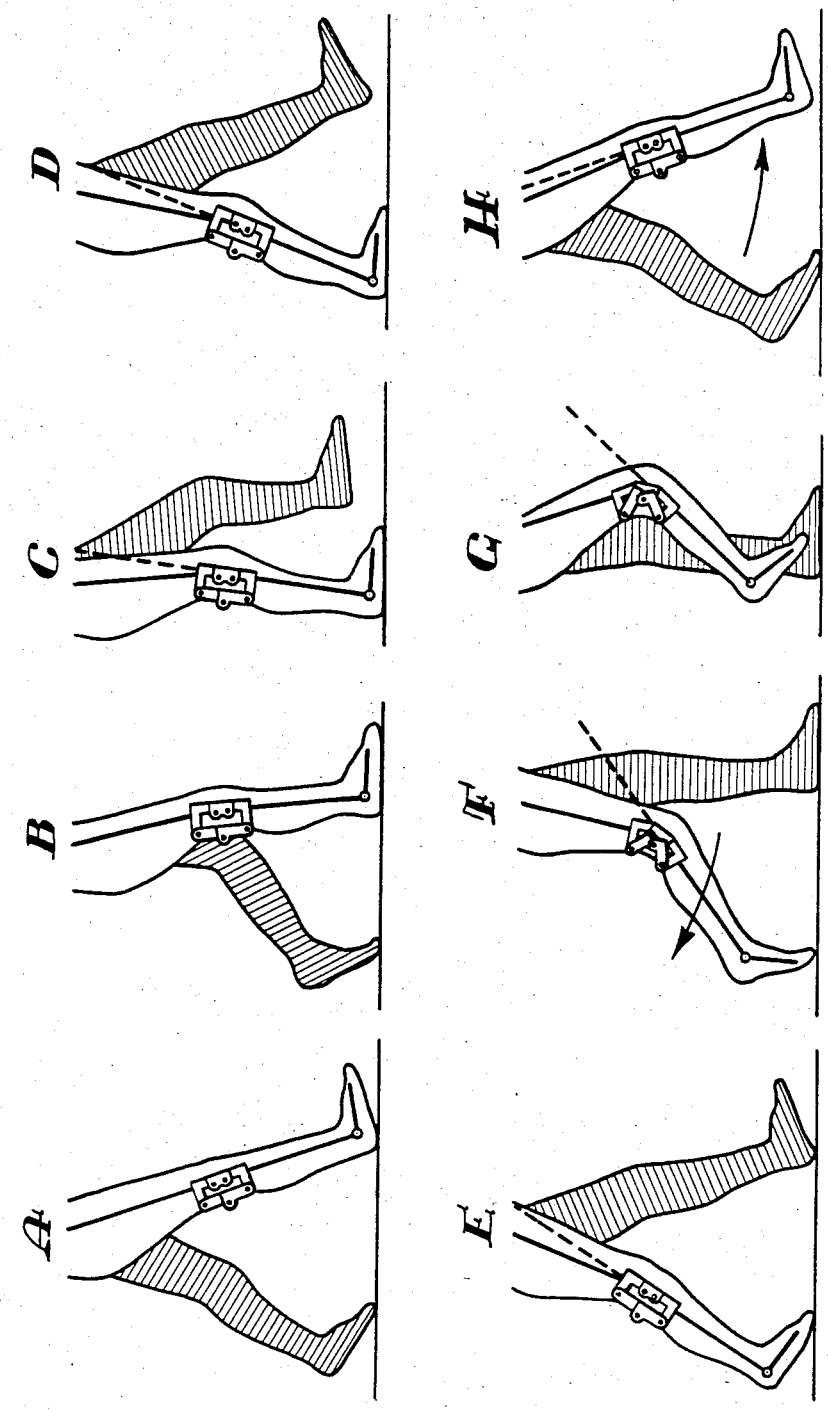
FIGS. 13 A through H show a number of sequential side views of a complete gait cycle being performed by a person who is wearing the mechanically controlled automatic releasing free knee brace of the present invention, which is illustrated partially schematically.

The present invention will be described in terms of a presently preferred embodiment with reference to the figures.

A perspective view of a mechanically controlled automatically releasing free knee brace made according to the principles of this invention is shown in FIG. 2. The brace comprises a thigh piece 22 for encircling the upper part of the leg of a patient and a leg piece 24 for encircling the lower leg of a patient. A lateral upper elongate member 26 and a medial upper elongate member 28 extend along the sides of the thigh piece 22 and are attached thereto. A lateral lower elongate member 30 and a medial lower elongate member 32 extend along the sides of the leg piece 24 and are attached thereto. The lateral upper elongate member 26 is coupled to the lateral lower elongate member 30 by a lateral polycentric hinge assembly 34 while the medial upper elongate member 28 is coupled to the medial lower elongate member 32 by a medial polycentric hinge assembly 36. A lock hinge assembly 38 is attached at one end to the lateral upper elongate member 26 near the lateral polycentric hinge assembly 34 and at the other end to the lateral lower elongate member 30 also near the lateral polycentric hinge assembly 34.

A foot piece 40 which extends in back of and under the foot of a patient is attached to the lower end of the leg piece 24 by means of an ankle hinge 42. Fastening straps extend around the open sides of the thigh piece 22, leg piece 24 and foot piece 40 and are provided with conventional closures so that the orthosis may be secured to the leg of a patient. The thigh piece 22 and leg piece 24 are open along the front and are both fabricated from a plastic material, which bends somewhat to comfortably accommodate the legs of a patient and to assist the installation and removal of the brace on a patient. The foot piece 40 is also fabricated from the same plastic material.

The present invention provides a lock hinge assembly 38 which automatically releases due to movements of the ankle and foot at appropriate times during the gait cycle so that the patient's knee may bend and normal gait may be approximated. To this end, the presently preferred embodiment of the present invention has a pull cable 44 which is connected to the lock hinge assembly 38 at one end. At the other end, the pull cable 44 is actuated by the operation of a range box 46 which is coupled to a throw arm 48 attached to a tongue 50 which extends from one side of the front of the foot piece 40 in the vicinity of the ankle and serves as the throw lever 52.

As will be described, during dorsiflexion of the ankle and subsequent plantar flexion of the foot near the end of a stance phase and the beginning of a swing phase of a gait cycle, forces are exerted through throw lever 52 on the throw arm 48, which, due to the operation of the range box 46, causes the pull cable 44 to be pulled unlocking the lock hinge assembly 38 and allowing the knee to bend during the swing phase of the gait cycle.

With reference now to the other figures in addition to FIG. 2, the construction and operation of the presently preferred embodiment of the present invention will be described in more detail.

The lateral and medial upper and lower elongate members 26, 28, 30 and 32 are preferably made of lightweight metal, such as aluminum, although other materials might be used. Members 26, 28, 30 and 32 will have slight curvatures to conform to the leg of a patient.

The ends of the lateral upper elongate member 26 and the lateral lower elongate member 30 terminate adjacent one another at the lateral polycentric hinge assembly 34 while the medial upper elongate member 28 and the medial lower elongate member 32 terminate adjacent one another at the medial polycentric hinge assembly 36. Only the lateral polycentric hinge assembly 34 is provided with a lock hinge assembly 38.

Referring to FIGS. 10 through 12, the construction and operation of a polycentric hinge and a lock hinge assembly will be described with reference to the lateral polycentric hinge assembly 34 and the lock hinge assembly 38.

The polycentric hinge assembly 34 comprises gear teeth 54 arcuately disposed on a first short member 55 affixed to the lower end of the lateral upper elongate member 26. First short member 55 has a first arcuately shaped end 57 provided with gear teeth 54 and a second end 59 provided with a yoke 61 into which the lower end of member 26 fits and is attached thereto by fastener 63. Corresponding gear teeth 56 are disposed on a second short member 65 affixed to the upper end of the lateral lower elongate member 30. Second short member 65 is similar to first short member 55 having an arcuate first end 67 with gear teeth 56 and a second end provided with a yoke 69 and is affixed to member 30 by fastener 61'.

The arcuate first end 57 of first short member 55 and the the arcuate first end 67 of second short member 65 are held between outer and inner hinge plates 58 and 60, respectively, so that the gear teeth 54 of first short member 55 mesh with the gear teeth 56 of second short member 65. As a result the lateral upper elongate member 26 and the lateral lower elongate member 30 rotate together.

A polycentric hinge such as lateral polycentric hinge assembly 34 has the characteristic that its pivot axis changes location as the angle between the members to which it is attached varies. A polycentric hinge is utilized in orthoses because the knee does not have a single axis of rotation as it is flexed. Instead, it has many such axes depending on the angle that the knee is flexed. Hence, polycentric hinges in general may more closely simulate the actual movement of a knee than do simple hinges having a single axis of rotation and provide a better fitting and operating orthosis.

Adjacent the outer and inner hinge plates 58 and 60, the first and second short members 55 and 65 each have a pair of arcuate surfaces, 62 and 64 respectively, corresponding to the pairs of arcuate surfaces 71 and 73 of the upper edges and lower edges of the hinge plates 58 and 60 respectively, the arcuate surfaces 62 and 64 complementing and moving along the arcuate surfaces 71 and 73 as the lateral upper and lower elongate members 26 and 30 are moved relative to one another.

An extension 75 on the anterior side of the outer and inner hinge plates 58 and 60 limits the movement of the lateral upper elongate members 26 and 30 with respect to one another so that in one direction their angle of rotation with respect to one another is limited to approximately a rectilinear orientation.

The medial polycentric hinge assembly 36 is similar in construction to the lateral polycentric hinge assembly 34 just described.

The lock hinge assembly 38 spans the lateral polycentric hinge assembly 34. Lock hinge assembly 38 comprises an upper offset arm 68 and a lower offset arm 70 which are affixed to the lateral upper elongate member 26 and the lateral lower elongate member 30 by fasteners 72 and 74, respectively.

The upper offset arm 68 is connected at its distal end 79 to an upper locking arm 76 provided with a yoke 81 fitting over end 79 by pivot pin 77 which defines a first axis of rotation 78 of the upper locking arm 76 about the upper offset arm 68. A lower locking arm 80 is similarly connected at its yoke 83 to the distal end 85 of the lower offset arm 70 by a second pivot pin 87 which defines a second axis of rotation 82 of the lower locking arm 80 about the lower offset arm 70.

Pivot pins 77 and 87 have pin portions which traverse bores in the upper offset arm 68 and the lower offset arm 70. These bores and pin portions are sized so that there is a small amount of play of the pins in these bores with the result that a small amount of relative rotation of the lateral upper and lower elongate members 26 and 30 respectively can take place, while the lock hinge assembly 38 remains in the locked state, as will be described. Thus, a small amount of flexing of the knee is enabled with the lock hinge assembly 38 in the locked state.

At its distal end, lower locking arm 80 is provided with a yoke portion 84 having a small posteriorly extending portion 86. The upper locking arm 76 is provided at its distal end with a tongue 88 having a small posteriorly extending portion 90. The upper and lower locking arms 76 and 80 and the yoke 84 and tongue 88 are configured in size so that tongue 88 fits within yoke 84 with the posteriorly extending portion 90 of tongue 88 being attached to the posteriorly extending portion 86 of yoke 84 by a pivot pin 89 which defines a central axis of rotation 92 about which the upper and lower locking arms 76 and 80 may rotate with respect to one another.

When upper locking arm 76 and lower locking arm 80 are in extension, i.e., are extended rectilinearly with respect to one another as shown in FIG. 10, the central axis of rotation 92 is located slightly posteriorly to the line connecting the first and second axes of rotation 78 and 82. In this position, lock hinge assembly 38 is in the locked position and the lateral upper elongate member 26 and lower elongate member 30 are oriented approximately rectilinearly with respect to one another and can only move a small amount relative to each other, the movement being restrained to the play in the pivot pins 77 and 87 in the bores located in the upper and lower offset arms 68 and 70.

When the leg is extended so that the upper and lower locking arms 76 and 80 are in extension and the lateral upper and lower elongate members 26 and 30 are approximately rectilinear, the lock hinge assembly 38 is in a locked state and is stable. This is because the central axis of rotation 92 is located posterior to the line connecting the first and second axes of rotation 78 and 82. A coiled tension spring 94 is stretched between a first point of attachment 96 located on the upper locking arm 76 and a second point of attachment 98 located on the lower locking arm 80. Spring 94 assists in stabilizing the lock hinge assembly 38 in the locked state. In addition, spring 94 causes the lock hinge assembly 38 to snap into the locked state when the orthosis is approaching the fully extended position but has not yet reached it, as will be described.

Alternately, a torsion spring could be used in place of coiled tension spring 94. This spring may be incorporated into the lock hinge assembly 38, minimizing possible interference with clothing.

The pull cable 44 is connected at one end to the lock hinge assembly 38 near the pivot pin 89 which defines the central axis of rotation 92. A pull exerted on pull cable 44 while the lock hinge assembly 38 is in the locked position overcomes the tension of spring 94 and moves the distal ends of the upper and lower locking arms 76 and 80 which are pivoted together at the central axis of rotation 92 anteriorly, causing the central axis of rotation 92 to move forward of the line joining the first and second axes of rotation 78 and 82. Accompanied by a force tending to bend the knee, the lock hinge assembly 38 goes into an unlocked state so that the lateral and medial upper elongate members 26 and 28 bend with respect to the lateral and medial lower elongate members 30 and 32, through operation of the lateral and medial polycentric hinges 34 and 36. This state is shown in FIG. 12.

The unlocking of the lock hinge assembly 38 is controlled by the range box 46 whose structure and operation can be understood with reference especially to FIGS. 2 through 9. Range box 46 in the presently preferred embodiment, is a long, hollow, rectangular box attached, to the lateral lower elongate member 30.

As can be seen most clearly in FIGS. 4 through 9 the range box 46 is longitudinally divided into a first channel 100 and a second channel 102 by two flat rectangular members 104 affixed to the lateral sides of the range box 46. Flat rectangular members 104 extend along only the middle portion of range box 46. A large central slot 106 separates the flat rectangular members 104.

A T-bar 108 having side branches 110 and a base portion 112 rides in the first and second channels 100 and 102 formed by the flat rectangular members 104, the side branches 110 being guided in the channels 100 and 102 by the flat rectangular members 104, the base portion 112 extending through the large central slot 106 between the flat rectangular members 104 when the side branches 110 of T-bar 108 are riding in the second channel 102.

The top end of range box 46 contains a directing block 114 which is biased by a pair of coiled springs 116 so that directing block 114 ordinarily presses against the ends of the flat rectangular members 104. Directing block 114 is located mostly in first channel 100 and is angled along its edge 118 which faces toward the flat rectangular members 104 so as to direct the side braches 110 of T-bar 108 into the second channel 102 from the first channel 100.

At the lower end of range box 46, situated mostly in the second channel 102, is the trigger block 120 which is similar in size and shape to the directing block 114, having an angled edge 124. A pair of coiled springs 122 biases the trigger block 120 against the ends of the flat rectangular members 104. Both the directing block 114 and trigger block 120 are preferably padded to reduce noise.

The pull cable 44 is connected at its second end to the trigger block 120 through a slot 126 in the posterior side of the range box 46 as shown in FIG. 2. As shown in FIG. 12, pull cable 44 is directed by a cable guide 123 so that a significant component of a force on cable 44 pulls the locking arms 76 and 80 anteriorly. A turnbuckle 125 is included for adjustment of the length of pull cable 44.

When trigger block 120 is moved against the pair of coiled springs 122 which normally biases it against the edges of the flat rectangular members 104, pull cable 44 pulls the upper and lower locking arm 76 and 80 forward destablizing the lock hinge assembly 38 so that the lock hinge assembly 38 is placed in an unlocked state and the polycentric hinge assemblies 34 and 36 are free to operate.

During a gait cycle, the T-bar 108 moves within the range box 46 between the first and second channels 100 and 102 as shown in FIGS. 5 through 9, 5a, and 8a. The base portion 112 of T-bar 108 is coupled to throw arm 48 by means of a ball and socket connector 128 which permits the orientation of the T-bar 108 to vary with respect to the throw arm 48. The ball and socket connector 128 may be of a type similar to that used in the throttle linkage of automobiles. During a gait cycle, as will subsequently be described in more detail, the side branches 110 of the T-bar 108 are caused by the throw arm 48 to move up from their position shown in FIG. 5 against the directing block 114 as shown in FIG. 6. The force on the throw arm 48 causes the side branches 110 to overcome the biasing of the pair of coiled springs 116 so that the side branches 110 of the T-bar 108 are directed from the first channel 100 past the ends of the flat rectangular members 104 into the second channel 102, the edge 118 of the directing block 114 helping to direct the side branches of T-bar 108 into the second channel 102, as shown in FIG. 7. Subsequent motion of the foot, as will be described, causes the throw arm 48 to begin pulling the T-bar 108 toward the bottom of range box 46 as shown in FIG. 8 until the side branches 110 of T-bar 108 press against the trigger block 120 overcoming the force of coiled spring 122 as shown in FIG. 9, thereby pulling on the pull cable 44 attached to trigger block 120. As the other end of pull cable 44 is connected to the lock hinge assembly 38, this motion places the lock hinge assembly 38 in the unlocked state as has been described. The edge 124 of trigger block 120 directs the side branches 110 of T-bar 108 back from the second channel 102 into the first channel 100, the pair of coiled springs 116 again pressing trigger block 120 against the edges of the flat rectangular members 104. The aforedescribed movement of the T-bar 108 within the range box 46 is repeated for each complete gait cycle.

It will be appreciated from the previous description of the operation of the range box that in order to unlock the lock hinge during each gate cycle, two events within the range box must sequentially take place: first, the side branches 110 of the T-bar 108 must press against the directing block 114 and be directed into the second channel 102 from the first channel 100; then the side branches 110 of the T-bar 108 must move in the opposite direction and press against the trigger block 120 to unlock the lock hinge assembly 38 while in the process being directed into the first channel 100. These events require that the ankle and foot pass through a certain range of movement comprising dorsiflexion and plantar flexion which explains the use of the term "range box." The range of required movement is adjustable, as will be described.

In the presently preferred embodiment of the present invention, foot piece 40 contains a forward extending tongue 50 forming the throw lever 52 in the vicinity of the ankle. Because of tongue 50, the foot piece 40 of the orthosis is situated, at the pivot 42, outside of the leg piece 24, rather than inside as is typically the case with locked-knee braces.

The throw arm 48 is connected at one end to the throw lever 52 by means of a yoke 130 having a pin through one of severals bores 127. Throw arm 48 comprises a stiff rod which can transmit the motion of the throw lever 52 as the ankle or foot moves to the range box 46, the other end of the throw arm 48 being connected to the ball and socket connection 128. The length of throw arm 48 may be adjusted by means of conventional adjusting nuts used at either or both ends.

The relation of the various positions of the leg and foot during a gait cycle to the movement of the T-bar 108 in the range box 46 and the resulting state of the lock hinge assembly 38 will now be described.

FIG. 13 illustrates significant points in the gait cycle and the function of the orthosis of the present invention. A complete gait cycle beginning with heel strike of the braced right leg is shown in FIG. 13A-13H. The orthosis of the present invention is shown partially schematically. At heel strike, as shown in FIG. 13A, the leg is in full extension and the lock hinge assembly 38 is in the locked state. The stability resulting from this locked state helps support the person. At this point, the side branches 110 of T-bar 108 are riding in the first channel 100. At "foot-flat", the position shown in FIG. 13B, the lock hinge assembly 38 and the knee remain locked. The side branches 110 of T-bar 108 remain in the first channel 100.

In FIG. 13C, as the opposite foot swings forward in front of the body, torque is placed on the knee and the knee bends slightly within the locked range of the lock hinge assembly 38, as has been described. The lock hinge assembly 38 remains in full extension and the side branches 110 of T-bar 108 remain in the first channel 100.

In FIG. 13D, adequate dorsiflexion of the right leg at the ankle has taken place forcing the side branches 110 of T-bar 108 against the directing block 114 to overcome the force of the pair of coiled springs 116 so that side branches 110 of the T-bar 108 are directed into the second channel 102 from the first channel 100. The lock hinge assembly 38 remains in full extension and the knee fully braced.

Subsequently, a plantar flexion motion begins as the heel is lifted off of the ground, as shown in FIG. 13E, causing the side branches 110 of the T-bar 108 to travel in the second channel 102 towards trigger block 120.

In FIG. 13F, plantar flexion has resulted in the side branches 110 of the T-bar 108 pressing against the trigger block 120 overcoming the force of the pair of coiled springs 122 and pulling on the pull cable 44 releasing the lock hinge assembly 38 so that both it and the knee may be flexed before the toe is finally lifted off of the ground. The side branches 110 of T-bar 108 are directed from the second channel 102 into the first channel 100.

During the swing phase of the gait cycle, the knee is free to bend as the lock hinge assembly remains unlocked as shown in FIG. 13G.

Toward the end of the swing cycle the knee moves toward full extension due in part to the momentum of the swinging leg and the lock hinge assembly 38 goes into the locked state, as shown in FIG. 13H. The spring 94 connecting the upper and lower locking arms 76 and 80 assist in the lock hinge assembly 38 achieving the locked state once the central axis of rotation 92 passes posterior to the line joining the first axis of rotation 78 and the second axis of rotation 82. Thus, the orthosis is prepared for heel strike and the repetition of the gate cycle beginning again with FIG. 13A.

It will be apparent from the foregoing description that the functioning of the orthosis of the present invention is dependent on adequate dorsiflexion of the leg at the ankle to cause the side branches 110 of the T-bar 108 to be directed from the first channel 100 to the second channel 102 followed by adequate plantar flexion to cause the side branches 110 of the T-bar 108 to press against and move the trigger block 120 and thereafter be directed back into the first channel 100. The positions during the gait cycle of any particular person at which the side branches 110 of the T-bar 108 will press against the directing block 114 and the trigger block 120 will depend on geometrical considerations, i.e., the length of the throw arm 48 and the length of the throw lever 52. These considerations are not independent and for example, a change in the length of the throw lever 52 will not equally affect the required angle of dorsiflexion and that of plantar flexion. While it is possible to compute the specific geometry required, in point of fact, trial and error experience with each individual will lead to rapid and accurate adjustment of the orthosis.

For example, if it is determined that the requisite angle of dorsiflexion is approximately correct but that the orthosis does not release, i.e., go into the unlocked state until too far past weight transfer, the throw lever 52 must be lengthened. This can be accomplished by attaching the throw arm 48 to a different bore in the throw lever 52. However, to some degree this will affect the angle of dorsiflexion. To restore the angle of dorsiflexion to its original value requires that the throw arm 48 then be shortened.

While the present invention has been described in terms of a presently preferred embodiment, it should be understood that many variations and modifications that are within the scope of the present invention may be used. For example, in the presently preferred embodiment, the range box 46 is attached to the lateral lower elongate member 30. However, it may also be attached to the leg piece 24 itself. In that case, the specific geometrical considerations would be different but the selections of the variables would be accomplished in the same manner.

In addition, other arrangements of components than those described with respect to range box 46 may be used.

Also, while the present invention has been described in terms of a preferred embodiment that provides an orthosis which is mechanically controlled, orthoses which use electro-mechanical or electrical components may be within the scope of the present invention. In particular, but not limited to such, orthoses which provide a means responsive to a preselected dorsiflexion followed by a preselected plantar flexion to effect release of the orthosis so that the leg may be more easily flexed are within the scope of the present invention.

It should also be pointed out that the preselected plantar flexion following the preselected dorsiflexion referred to herein could in fact, in any particular case, include a smaller dorsiflexion rather than a plantar flexion in the absolute sense, should the anatomy or condition of any particular patient make such desirable. Such is still within the application of the principles described, and hence the scope of the present invention.

Thus, it should be appreciated that there are many modifications and variations of the described presently preferred embodiment that are within the scope of the invention and the claims should be interpreted accordingly.

I claim:

1. An orthosis for the leg comprising:
a first elongate member adapted to be secured along the side of the upper part of the leg above the knee;
a second elongate member adapted to be secured along the side of the lower part of the leg below the knee;
a pivot means interconnecting one end of the first elongate member with one end of the second elongate member, said pivot means adapted for placement adjacent the knee at the side thereof for providing relative pivotal movement of the first and second elongate members about a generally horizontal axis at the knee when the upper and lower parts of the leg are moved relative to one another in a flexing or extending motion at the knee;
a locking means for locking said pivot means when the upper and lower parts of the leg are moved relative to one another in an extending motion a predetermined amount, said locking means restricting the motion of said first and second elongate members with respect to one another; and
means for unlocking said locking means so that said first and second elongate members may pivot about said axis and said upper and lower parts of the leg may be moved relative to one another in a flexing motion, said means responsive to a predetermined dorsiflexion of the ankle followed by a predetermined plantar flexion of the ankle during a single gait cycle.

2. An orthosis as in claim 1 wherein said pivot means comprises a polycentric hinge.

3. An orthosis as in claim 1 wherein said locking means comprises:
a first locking arm member pivotably secured at its first end at a first position which moves with said first elongate member;
a second locking arm member pivotably secured at its first end at a second position which moves with said second elongate member;
the second ends of said first and second locking arm members being pivotably attached to one another at a third position near their second ends, said first and second locking arm members being extendable approximately rectilinearly to lock said locking means when said third position is posterior to the line joining said first and second positions with respect to the front of the knee, said locking means being unlocked when said third position is anterior to the line joining said first and second positions.

4. An orthosis as in claim 3 wherein said means for unlocking includes a means for moving said third position anterior to the line joining said first and second positions.

5. An orthosis as in claim 4 wherein said means for moving said third position includes a cable attached to at least one of said locking arms for pulling on said locking arms so that said third position is moved anterior to the line joining said first and second positions, said means for unlocking also including a means for pulling on said cable.

6. An orthosis as in claim 1 wherein said means for unlocking comprises:
a first selectively enabled means coupled to said locking means for unlocking said locking means, said first selectively enabled means responsive to a predetermined plantar flexion of the ankle to unlock said locking means when said first selectively enabled means is selectively enabled; and
a second selectively enabling means for selectively enabling said first selectively enabled means, said second selectively enabling means responsive to a predetermined dorsiflexion of the ankle to enable said first selectively enabled means.

7. An orthosis as in claim 1 wherein said means for unlocking comprises:
a guideway fixedly secured with respect to said second elongate member having first and second portions;
a switch means located proximate to said second portion of said guideway coupled to said locking means for unlocking said locking means when said switch means is actuated;
a sliding means for slidably moving along said guideway, said sliding means including an actuating means for actuating said switch means when said sliding means slides proximate to said switch means;
a first linkage means for coupling said sliding means and a point which moves with said foot, the movement of said ankle in dorsiflexion or plantar flexion causing said sliding means to move in said guideway; and
a first directing means for directing said sliding means from said first portion to said second portion of said guideway when said ankle has moved a predetermined amount in dorsiflexion.

8. An orthosis as in claim 7 further comprising a second directing means for directing said sliding means from said second portion to said first portion when said foot has moved a predetermined amount in plantar flexion.

9. An orthosis as in claim 8 wherein said switch means includes:
a movable block;
a second linkage means connected to said block and to said means for locking, said second linkage means for unlocking said locking means when said block is moved; and biasing means for pressing on said block so that said block at least partially obstructs said second portion of said guideway, said biasing means overcomeable by said actuating means pressing on said block and moving said block against said biasing means when said sliding means slides proximate to said switch means.

10. An orthosis as in claim 8 wherein said first and second portions of said guideway comprise first and second channels respectively, said first and second channels located side by side and communicating with one another at first and second locations, and wherein said first directing means is located proximate to said first location and said second directing means is located proximate to said second location.

11. An orthosis as in claim 10 wherein said first linkage means includes a rod assembly coupled adjacent its first end to said sliding means and adjacent its second end to said point which moves with said foot.

12. An orthosis as in claim 11 including a member adapted to move with said foot, said member having an arm extending anterior to said ankle, said arm for attachment to the second end of said rod assembly whereby dorsiflexion or plantar flexion of said ankle moves said rod assembly causing said sliding means to move in said guideway.

13. An orthosis as in claim 12:

wherein said second directing means includes a surface angled toward said first channel from said second channel, said surface directing said sliding means from said second channel into said first channel when said sliding means slides in said second channel along said surface; and wherein said switch means includes:

a first movable block on which said surface is located;

a second linkage means connected to said first movable block and to said means for locking, said second linkage means for unlocking said locking means when said first block is moved; and means for biasing said first block so that said first block at least partially obstructs said second channel, said means overcomeable by said sliding means when said sliding means is moving in said second channel against said first block to unlock said locking means, said first block preventing said means for sliding from moving into said second channel from said first channel at said second location.

14. An orthosis as in claim 13 wherein said locking means comprises:

a first locking arm member pivotably secured at its first end in a first position which moves with said first elongate member;

a second locking arm member pivotably secured at its first end at a second position which moves with said second elongate member;

the second ends of said first and second locking arm members being pivotably attached to one another at a third position near their second ends, said first and second locking arm members being extendable approximately rectilinearly to lock said locking means when said third position is posterior to the line joining said first and second positions with respect to the front of the knee, said locking means being unlocked when said third position is anterior to the line jointing said first and second positions;

said second linkage means being attached to at least one of said locking arms, said second linkage means moving said third position anterior to the line joining said first and second positions when said first movable block is moved by said sliding means.

15. An orthosis as in claim 14 wherein said first directing means includes a surface angled toward said second channel from said first channel, said surface directing said sliding means from said first channel into said second channel when said sliding means slides in said first channel along said surface.

16. An orthosis as in claim 15 wherein said first directing means includes:

a movable block on which said surface is located;

means for biasing said block, said means overcomeable by said sliding means for pressing when said sliding means is moving in said first channel toward said block, said block preventing said means for sliding from moving into said first channel against said second channel at said first location.

17. An orthosis as in claim 14 wherein said linkage means includes a cable.

18. An orthosis as in claim 11 wherein said means for sliding includes a T-Bar, the branches of which slide in said first and second channels and the base of which is coupled to said rod assembly.

19. In an orthosis for the leg of the type which includes a first member adapted to be secured to the upper part of the leg, a second member adapted to be secured to the lower part of the leg, and a pivotable mechanism coupling said first and second members for placement adjacent the knee, said orthosis automatically locking the first and second members in a state of relatively greater resistance to movement with respect to one another during a portion of the gait cycle in order to secure the leg in a generally extended state and automatically unlocking the first and second members to place them in a state of relatively lesser resistance to movement with respect to one another during another portion of the gait cycle so that the leg is permitted to flex at the knee, the improvement comprising:

means for unlocking said first and second members at a predetermined plantar flexion of the ankle, said means responsive to a sequence during each gait cycle of a predetermined dorsiflexion of the ankle followed by said predetermined plantar flexion.

* * * * *